United States Patent [19]
Delmage et al.

[11] Patent Number: 6,124,259
[45] Date of Patent: Sep. 26, 2000

[54] METHOD FOR TREATING OPHTHALMIC DISORDERS WITH IGFBP

[75] Inventors: Michael J. Delmage, Scotts Valley; Andreas Sommer, Pleasanton, both of Calif.

[73] Assignee: Celtrix Pharmaceuticals, Inc., San Jose, Calif.

[21] Appl. No.: 09/080,366

[22] Filed: Feb. 24, 1998

Related U.S. Application Data

[63] Continuation of application No. 08/606,271, Feb. 23, 1996, abandoned, which is a continuation of application No. 08/203,688, Feb. 28, 1994, abandoned, which is a continuation of application No. 08/011,652, Jan. 28, 1993, abandoned.

[51] Int. Cl.[7] ........................... A61K 38/27; A61K 38/28
[52] U.S. Cl. ........................... 514/12; 530/350; 530/324; 435/69.1
[58] Field of Search ........................... 514/12; 530/350, 530/324; 435/69.1

[56] References Cited

U.S. PATENT DOCUMENTS

| | | | |
|---|---|---|---|
| 3,773,919 | 11/1973 | Boswell et al. | |
| 5,187,151 | 2/1993 | Clark et al. | 514/3 |
| 5,200,509 | 4/1993 | Spencer et al. | 530/350 |
| 5,407,913 | 4/1995 | Sommer et al. | 514/121 |

FOREIGN PATENT DOCUMENTS

| | | |
|---|---|---|
| 0369943 | 5/1990 | European Pat. Off. |
| WO 89/08667 | 9/1989 | WIPO . |
| 89/09792 | 10/1989 | WIPO . |
| WO 89/09792 | 10/1989 | WIPO . |
| WO 90/13302 | 11/1990 | WIPO . |
| WO 92/18154 | 10/1992 | WIPO . |

OTHER PUBLICATIONS

Robert Baxter et al "Growth Hormone Dependent Insulin Like Growth Factor (IGF) Binding Protein From Human Plasma Differs From Other Human IGF Binding Proteins" Biochemical and Biophysical Research Communications, vol. 139, No. 3, pp. 1256–1261, 1986.

Wiedemann, "Growth Factor in Retinal Diseases: Proliferature Diabetic Retinopathy, and Retinal Degeneration" Survey of Ophthalmology, vol. 36, No. 5, pp. 375–384, 1992.

Shunichi Shimasaki et al., "Identification and Molecular Characterization of Insulin Like Growth Factor Binding Proteins (IGFBP–1, –2, –3, –4, –5 and 6)" Progress in Growth Factor Research, vol. 3, pp. 243–266, 1991.

Barritault et al. "Is There a Ubiquitous Growth Factor in the Eye? Proliferation Induced in Different Cell Types by Eye–Derived Growth Factors" *Differentiation* (1981) 18:29–42.

Baxter et al. "Growth hormone–dependent insulin–like growth factor (IGF) binding protein from human plasma differs from other human IGF binding proteins" *Biochem. Biophys. Res. Comm.* (1986) 139(3):1256–1261.

Binkert et al., "Cloning, sequence analysis and expression of a cDNA encoding a novel insulin–like growth factor binding protein (IGFBP–2)" *EMBO Journal* (1989) 8(9):2497–2502.

Blum et al. "Plasma IGFBP–3 levels as clinical indicators" Spencer, E.M., ed., Modern Concepts in Insulin–Like Growth Factors, Elsevier, New York, (1991) pp. 381–393.

Brewer et al. "Cloning, Characterization, and Expression of a Human Insulin–like Growth Factor Binding Protein" *Biochem. Biophys. Res. Comm.* (1988) 152(3):1289–1297.

Busby et al. "Purification of a 31,000–Dalton Insulin–like Growth Factor Binding Protein from Human Amniotic Fluid Isolation of Two Forms with Different Biologic Actions" *J. Biol. Chem.* (1988) 263(28):14203–14210.

Chen et al. "Angiogenic activity of vitreous and retinal extract" *Assoc. Res. Ophthal.* (1980) 19(6):596.

D'Amore et al. "Endothelial Cell Mitogens Derived from Retina and Hypothalamus: Biochemical and Biological Similarities" *J. Cell. Biol.* (1984) 99:1545–1549.

Deitz, M.D. et al. "Progressive Hyperopia in Radial Keratotomy" *Ophthalmology* (1986) 93(10):1284–1289.

Dills et al. "Association of elevated IGF–I levels with increased retinopathy in late–onset diabetes" *Diabetes* (1991) 40:1725–1730.

Drop et al. "Immunoassay of a somatomedin–binding protein form human amniotic fluid: levels in fetal, neonatal, and adult sera" *J. Clin. Endocrin. Met.* (1984) 84:908–915.

Elgin et al. "An insulin–like growth factor (IGF) binding protein enhances the biologic response of IGF–I" *Proc. Natl. Acad. Sci. USA* (1987) 84:3254–3258.

Elstow et al. "Bovine Retinal Angiogenesis Factor Is a Small Molecule (Molecular Mass<600)" *Invest. Ophthalmol. Vis. Sci.* (1985) 26(1):74–79.

Feeney–Burns et al. "Aging Human RPE: Morphometric Analysis of Macular, Equatorial, and Peripheral Cells" *Invest. Ophthalmol. Vis. Sci.* (1984) 25(2):195–200.

Frank, R.N. "On the pathogenesis of diabetic retinopathy" *Opthalmol.* (1990) 98:586–593.

Fredj–Reygrobellet et al. "Acidic FGF and other growth factors in preretinal membranes from patients with diabetic retinopathy and proliferative vitreoretinopathy" *Opthalm. Res.* (1991) 23:154–161.

Gass, M.D. "Idiopathic Senile Macular Hole, Its Early Stages and Pathogenesis" *Arch. Ophthalmol.* (1988) 106:629–639.

(List continued on next page.)

*Primary Examiner*—F. T. Moezie
*Attorney, Agent, or Firm*—Morrison & Foerster, L.L.P.

[57] ABSTRACT

This is a method for treating ophthalmic disorders associated with an excess of IGF-I or IGF-II. The method comprises administering individuals with an IGF excess insulin-like growth factor binding protein (IGFBP). The preferred form is IGFBP-3.

14 Claims, No Drawings

OTHER PUBLICATIONS

Glaser, M.D. et al. "The Demonstration of Angiogenic Activity from Ocular Tissues" *Ophthalmology* (1980) 87(5):440–446.

Grant et al. "Insulin–Like Growth Factors in Vitreous, Studies in Control and Diabetic Subjects with Neovascularization" *Diabetes* (1966) 35:416–420.

Grant et al. "Insulin–like growth factor I stimulates proliferation, migration, and plasminogen activator release by human retinal pigment epithelial cells" *Curr. Eye Res.* (1990) 9:323–335.

Hjelmeland et al., "Growth factors: soluble mediators of wound repair and ocular fibrosis", *March of Dimes Birth Defects Compendium*, 2nd Ed., pp. 87–101.

Hyldahl, "Control of Cell Proliferation in the Human Embryonic Cornea: An Autoradiographic Analysis of the Effect of Growth Factors on DNA Synthesis in Endothelial and Stromal Cells in Organ Culture and After Explanation In Vitro" *J. Cell. Sci.* (1986) 83:1–21.

Karas et al. "Restenosis following coronary angioplasty" *Clin. Cardiol.* (1991) 14:791–801.

King et al. "Receptors and growth–promoting effects of insulin–like growth factors on cells from bovine retinal capillaries and aorta" *J. Clin. Invest.* (1985) 75:1028–1036.

Knauer et al. "Purification and characterization of multiplication–stimulating activity (MSA) carrier protein" *J. Supramol. Struct. Cell. Biochem.* (1981) 15:177–191.

Kuffer et al. "Partial purification of a specific inhibitor of the insulin–like growth factors by reversed–phase high–performance liquid chromatography" *J. Chromophotog.* (1984) 336:87–92.

Langer et al. "Biocompatibility of polymeric delivery systems for macromolecules" *J. Biomed. Mater. Res.* (1981) 15:267–277.

Langer et al. "Isolation of a Cartilage Factor That Inhibits Tumor Neovascularization" *Science* (1976) 193(4247):70–72.

Leschey et al. "Growth factor responsiveness of human retinal pigment epithelial cells" *Invest. Ophthalmol. Vis. Sci.* (1990) 31(5):839–846.

Maack et al. "Molecular genetics and actions of recombinant insulin–like growth binding protein–3" Spencer, E.M., ed., *Modern Concepts in Insulin–Like Growth Factors*, Elsevier, New York, (1991) pp. 715–728.

Martin et al. "Insulin–like Growth Factor–binding Protein from Human Plasma" *J. Biol. Chem.* (1986) 261(19):8754–8760.

McAvoy et al. "Growth factors in the eye" *Prog. Growth Factor Res.* (1990) 2:29–43.

Merimee et al. "Insulin–Like Growth Factors, Studies in Diabetics with and without Retinopathy" *N. Engl. J. Med.* (1983) 309(9):527–529.

Morse et al. "Bovine retinal pigment epithelium promotes proliferation of choroidal endothelium in vitro" *Arch. Ophthalmol.* (1989) 107:1659–1663.

Raymond et al. "Isolation and Identification of Stimulatory and Inhibitory Cell Growth Factors in Bovine Vitreous" *Exp. Eye Res* (1982) 34: 267–286.

Ruelius–Altemose et al. "Further Studies on Inhibition and Stimulation of Vascular Endothelial Cell Growth" *Invest. Ophthalmol. Vis. Sci.* (1985) (ARVO Suppl) 26(3):25.

Shimasaki et al. "Identification of Five Different Insulin–like Growth Factor Binding Proteins (IGFBPs) from Adult Rat Serum and Molecular Cloning of a Novel IGFBP–5 in Rat and Human" *J. Biol. Chem.* (1991) 266(16):10646–10653.

Shimasaki et al. "Isolation and Molecular Cloning of Insulin–Like Growth Factor–Binding Protein–6" *Mol. Endocrinol.* (1991) 5(7):938–948.

Shimasaki et al. "Molecular Cloning of the cDNAs Enclod-ing a Novel Insulin–Like Growth Factor–Binding Protein from Rat and Human" *Mol. Endocrinol.* (1990) 4(10):1451–1458.

Sidman et al. "Controlled Realease of Macromolecules and Pharmaceuticals from Synthetic Polypeptides Based on glutamic Acid" *Biopolymers* (1983) 22(1):547–556.

Sommer et al. "Molecular genetics and actions of recombinant insulin–like growth factor binding protein–3" International Symposium on Insulin–Like Growth Factors/Somatomedins, San Francisco, CA, Modern Concepts of Insulin–Like Growth Factors, (1991) E. M. Spencer, ed., Elsevier, New York, 715–728.

Waring et al. "Stability of refraction During Four Years After Radial Keratotomy in the Prospective Evaluation of Radial Keratotomy Study" *Am. J. Ophthalmol.* (1991) 111:133–144.

Weller et al. "Prolifertive vitreoretinopathy—is it anything more than wound healing at the wrong place?"*Int. Ophthalmol.* (1990) 14:105–117.

Wiedemann, P. "Growth factors in retinal diseases: proliferative vitreoretinopathy, proliferative diabetic retinopathy and retinal degeneration" *Surv. Opthalmol.* (1992) 36:373–384.

Wood et al. "Cloning and Expression of the growth hor-mone–dependent insulin–like growth factor–binding protein" *Mol. Endocrin.* (1988) 2:1176–1185.

Zapf et al. "Pathophysiological and clinical aspects of the insulin–like growth factors" *Hormone Res.* (1986) 24:160–165.

METHOD FOR TREATING OPHTHALMIC DISORDERS WITH IGFBP

This application is a continuation of U.S. patent application Ser. No. 08/606,271, filed Feb. 23, 1996, now abandoned, which is a continuation of U.S. patent application Ser. No. 08/203,688, filed Feb. 28, 1994, now abandoned, which is a continuation of U.S. patent application Ser. No. 08/011,652, filed Jan. 28, 1993, now abandoned.

DESCRIPTION

1. Technical Field

This invention relates to the treatment of ophthalmic disorders. This invention is a medical treatment for ophthalmic conditions which are associated with an excess of insulin-like growth factor (IGF) and excessive proliferation of tissue. The method comprises administering an insulin-like growth factor binding protein (IGFBP).

2. Background Art

Growth factors are polypeptides which stimulate a wide variety of biological responses (e.g., DNA synthesis, cell division, cell differentiation, expression of specific genes, etc.) in a defined population of target cells. A variety of growth factors have been identified including transforming growth factor-$\beta_1$ (TGF-$\beta_1$), TGF-$\beta_2$, TGF-$\beta_3$, epidermal growth factor (EGF), platelet-derived growth factor (PDGF), fibroblast growth factor (FGF), insulin-like growth factor-I (IGF-I), and IGF-II.

IGF-I and IGF-II are related in amino acid sequence and structure, with each polypeptide having a molecular weight of approximately 7500 daltons. IGF-I mediates the major effects of growth hormone and thus is the primary mediator of skeletal growth after birth. IGF-I has also been implicated in the actions of various other growth factors, since treatment of cells with such growth factors leads to increased production of IGF-I. In contrast, IGF-II is believed to have a major role in fetal growth. Both IGF-I and IGF-II have insulin-like activity (hence the name) and are mitogenic (stimulating cell division) for various types of cells involved in the growth and differentiation of skeletal tissues such as muscle and bone, as well as non-skeletal tissues.

IGF can be measured in blood serum to diagnose abnormal growth-related conditions, e.g., pituitary gigantism, acromegaly, dwarfism, various growth hormone deficiencies, etc. Although IGF is produced in many tissues, most circulating IGF is believed to be synthesized in the liver.

Unlike most growth factors, the IGFs are present in substantial quantity in the circulation, but only a very small fraction of this IGF is free in the circulation or in other body fluids. Most IGF is complexed with IGF-binding proteins. IGF in the blood is mainly complexed with IGFBP-3, the major circulating IGF-binding protein.

Almost all IGF circulates in a non-covalently associated ternary complex composed of IGF-I or -II, an IGF specific binding protein termed IGFBP-3, and a larger protein termed the Acid Labile Subunit (ALS). This ternary complex is composed of equimolar amounts of each of the three components. The ALS has no direct IGF binding activity and appears to bind only a preformed IGF/IGFBP-3 complex. The ternary complex of IGF+IGFBP-3+ALS has a molecular weight of approximately 150,000 daltons. This ternary complex likely functions in the circulation "as a reservoir and a buffer for IGF-I and IGF-II preventing rapid changes of free IGF." Blum, W. F., et al., "Plasma IGFBP-3 Levels as Clinical Indicators", In *Modern Concepts in Insulin-Like Growth Factors,* E. M. Spencer, ed., Elsevier, New York, pages 381–393, 1991.

Having most circulating IGF in complexes is very beneficial. Excess free IGF can cause serious hypoglycemia because IGF has insulin-like effects on circulating glucose levels. In contrast to the low levels of free IGFs and IGFBP-3, there is a substantial pool of free ALS in plasma which assures that IGF/IGFBP-3 complex entering the circulation immediately forms a ternary complex.

IGFs bound to IGFBPs do not readily diffuse through capillary walls (Drop et al. *J. Clin Endocrin. Met.* (1984) 84:908–15.) The blood-ocular barrier is a formidable barrier to many chemicals. The blood-ocular barrier forms during fetal development. Before the barrier forms, serum proteins, including many growth factors such as IGF's and IGFBP's, travel freely from the blood into the eye where they effect development and differentiation of eye structures. At about four to five months for human fetuses, the blood-ocular barrier is formed by tight junctions in three layers: the RPE, the endothelium lining of the capillaries of the retina and iris, and the epithelium of the ciliary body. Tripathi et al. *Amer. J. Anatomy* (1991) 192:442–71. After the blood-ocular barrier forms, and as long as the barrier is intact, no large proteins such as IGFs or IGFBP-s leave the blood to enter ocular structures.

Nevertheless, IGF-I and IGF-II have been found in the eye in excess in certain ophthalmic disorders. Binding of circulating IGF-I to retinal endothelial cells increases DNA synthesis and promotes chemotaxis. King et al., *J. Clin. Invest.* (1985) 75:1028–36; and Morse et al. *Arch. Ophthalmol.* (1989) 107:1659–63.

Retinal pigment epithelial (RPE) cells and the neural retina have receptors for IGF-I and IGF-II. When human RPE cells are cultured, they express very little IGF-I and almost no IGF-II mRNA, indicating an ability to produce little, if any, IGF. Hence it has been hypothesized that IGF-I or IGF-II associated with RPE cells comes from the circulation, and not from local production by RPE cells. Martin et al., *Mol. Brain Res.* (1992) 12:181–86.

Leschey et al. recently questioned the role of IGF-I in inducing migration and proliferation of RPE cells. Leschey et al. tested the effects of several growth factors on density-arrested human RPE cells in tissue culture. Leschey et al. reported that IGF-I, PDGF and insulin "were weak or modest stimulators when used alone." The combination of insulin (representing IGF-I), PDGF, FGF and EGF was synergistic, yielding more thymidine incorporation than the sum of the peak yields of each of these factors alone. IGF-I itself was not tested in combination. Leschey pointed out that RPE cells may respond differently from epithelial cells, because RPE cells have a neural ectodermal origin. (*Invest. Ophthalmol. Vis. Sci.* (1990) 31:839–846).

IGF Binding Proteins

IGFBP-3 is the most abundant IGF binding protein in the circulation. Recently, Wood et al. (*Mol. Endocrin.* (1988), 2:1176–85) and Spratt et al. (*Growth Factors* (1990), 3:73–72) described the cloning and expression of human IGFBP-3. The gene for IGFBP-3 codes for 291 amino acids, the first 27 of which represent a characteristic signal sequence. Thus, the mature protein comprises 264 amino acids and has a predicted molecular weight of 28,749 (without glycosylation or other post-translational changes). When the human IGFBP-3 gene was expressed in Chinese hamster ovary ("CHO") cells and the conditioned culture medium was subjected to SDS electrophoresis and transferred to nitrocellulose membrane, Spratt et al. reported "the presence of a 43–45-kd doublet [protein band], a 28 kd band and a minor 31 kd band," (p. 69) indicating there were post-translational changes. This pattern is seen in serum, suggesting a similar range of post-translational changes in humans.

It is unclear which tissue is the primary source of circulating IGFBP-3, although synthesis has been demonstrated in numerous cell types, including human fibroblasts, liver cells (most likely Kupfer cells) and osteoblasts. cDNA libraries that include the IGFBP-3 cDNA have been obtained from liver and other tissues. Vascular endothelial cells produce IGFBP-3 and may be the major source for systemic IGFBP-3. Recently, Waldbillig et al. reported that monkey retinal pigment epithelial cells in tissue culture synthesize, secrete and degrade insulin-like growth factor binding proteins which may be IGFBP-3. *J. Cell. Physiol.* (1992) 150:76–83)

IGFBP-3 has been purified from natural sources and produced by recombinant means. For instance, IGFBP-3 can be purified from natural sources using a process such as that shown in Martin and Baxter (*J. Biol. Chem.* (1986) 261:8754–60). IGFBP-3 also can be synthesized by recombinant organisms as discussed in Sommer, A. et al., In *Modern Concepts of Insulin-Like Growth Factors,* E. M. Spencer, ed., Elsevier, New York, pp. 715–728, 1991. This recombinant IGFBP-3 binds IGF-I with a 1:1 molar stoichiometry.

At least five other distinct IGF binding proteins have been identified in various tissues and body fluids. Although all these proteins bind IGFs, they each originate from separate genes and they have distinct amino acid sequences. Thus, the binding proteins are not merely analogs of a common precursor. For example, Spratt et al. compared the amino acid sequences of IGFBP-1, -2 and -3. Of the total 264 amino acids in the mature protein, only 28% of the amino acids are identical between IGFBP-3 and IGFBP-1, and 33% are identical between IGFBP-3 and IGFBP-2. Spratt et al. suggested that the similar portions of the binding proteins are the region(s) that bind IGF. Unlike IGFBP-3, the other IGFBPs in the circulation are not saturated with IGFs. It appears that the lower saturation of the other IGFBPs in the circulation is due to excess binding capacity. None of the IGF binding proteins other than IGFBP-3 can form the 150 KD circulating ternary complex. All six known IGFBPs are reviewed and compared by Shimasaki and Ling, *Prog. Growth Factor Res.* (1991) 3:243–66.

Ophthalmic Disorders

Major ophthalmic disorders affect the posterior segment, including the retina and lens, as well as the anterior segment which includes the cornea, conjunctiva and sclera. Among the most important posterior segment disorders are macular holes and degeneration, retinal tears, diabetic retinopathy, vitreoretinopathy and miscellaneous disorders. The most important disorder of the lens is cataracts. The most important disorders of the cornea are refractive disorders such as the sequelae of radial keratotomy), dry eye, viral conjunctivitis, ulcerative conjunctivitis and wound healing (such as corneal epithelial wounds) and the consequences of Sjögren's syndrome. These are discussed briefly below.

Macular Hole

Macular holes produce blurred central vision, or metamorphopsia. The cause of most macular holes is unknown. However, trauma, cystic degeneration and vitreoretinal traction have all been associated with macular hole formation. Full thickness holes also appear following myopic degeneration, laser photocoagulation, lightning strike and pilocarpine administration. There also is a higher frequency of macular holes after cataract extraction.

The idiopathic senile macular hole is a disorder occurring generally in healthy women who are in their sixth decade of life or beyond. The more severe holes involve the full thickness of the macula and are surrounded by a halo of retinal detachment. In the early stage, there may be a sudden decrease or distortion in vision. But early changes are difficult for physicians to spot. Patients may experience sudden vision changes or may not notice symptoms if the condition slowly evolves. Some experts believe that macular holes begin with central or foveolar detachment, which eventually develops into a full-depth macular hole. See, Gass, "Idiopathic Senile Macular Hole—Its Early Stages and Pathogenesis", *Arch. Ophthalmol.,* 108:629–639 (1988). Partial holes, that is, holes which are partial in depth or in shape, i.e., having a new moon or horseshoe shape, are not readily observed but are worth diagnosing before they progress to full-thickness holes, particularly if an effective way to stop progression to macular holes were to become available.

There has been no effective treatment for macular holes of unknown origin. Certain operations, such as trans-pars plana vitrectomy, may interrupt the progress of macular degeneration toward full-thickness hole formation. However, the surgery may permanently damage central vision.

Macular Degeneration

Age-related macular degeneration (AMD) is the major cause of severe visual loss in the elderly. Most AMD patients have a build-up of fibrous deposits in the macula and retina and atrophy of the retinal pigment epithelium. The retinal pigment cells are long-lived. They scavenge for photoreceptor discs from the rods and cones for years and accumulate intracellular wastes. The incompletely digested residues reduce cytoplasmic space (Feeny-Burns, L. et al., *Invest. Ophthal. Mol. Vis. Sci.* 25:195–200 (1984)). As the cell volume available to the metabolically active organelles diminishes, the capacity to digest photoreceptors decreases, and this may be the basis for macular degeneration.

Some patients also experience exudative AMD with choroidal neovascularization, detachment and tears of the retinal pigment epithelial detachment, retinal pigment epithelial tears, fibrovascular disciform scarring, and vitreous hemorrhage.

Subretinal neovascularization (SRN) also may accompany AMD. Generally, SRN means the growth of new blood vessels beneath the retina. These abnormal vessels may lie between the choroid and the retinal pigment cells or between the retina and the retinal pigment cells.

Subretinal neovascularization is also related to the disciform process. A disc-shaped subretinal fibrovascular membrane is usually located in the macular region, whose deterioration has been responsible for more than 80% of cases of significant visual loss in patients with age related macular degeneration. The disciform process results from disease processes which affect the RPE-Bruch's brainchoriocapillaris complex.

Retinal Tears

The retina may tear or separate from the choroid, and the choroid may rupture, for a wide variety of reasons. A frequent cause is mechanical trauma either to the eye or other parts of the head.

Other situations in which tissue separation is observed include such widely disparate conditions as detachment of retina and pigment epithelium, degenerative myopia, as may be evidenced by visible breaks in Bruch's membrane (lacquer cracks), acute retinal necrosis syndrome (ARN), and traumatic chorioretinopathies or contusion (Purtscher's Retinopathy).

Other Retinal Disorders

There are a variety of retinal disorders, whose current treatment is not optimal. The retina may tear, form holes and separate from the underlying choroid due to lack of fibrous or supporting tissue.

Other retinal disorders include edema and ischemic conditions. Macular and retinal edema which are often associated with metabolic illnesses such as diabetes mellitus (see below). Edema is also found with accelerated or malignant hypertension. Macular edema is a common complication of prolonged inflammation due to uveitis, Eales disease, or other diseases. Local edema is associated with multiple cytoid bodies ("cotton bodies") as a result of AIDS.

Retinal ischemia can occur from either choroidal or retinal vascular diseases, such as central or branch retinal vein occlusion, collagen vascular diseases and thrombocytopenic purpura. Retinal vasculitis and occlusion is seen with Eales disease and systemic lupus erythematosus.

Diabetic Retinopathy

Dills et al. (*Diabetes* (1991) 40:1725–20) disclosed that in the serum of a large group of diabetics, "higher levels of IGF-I were significantly associated with an increased frequency of proliferative diabetic retinopathy (PDR)." However, vitreous or retinal concentrations of IGF-I may be even more important than systemic levels.

Sebag and McMeel reviewed the pathogenesis of PDR. The initiating event may be inadequate tissue oxygenation which causes vasodilation. Inadequate oxygenation may occur after the arterial basement membrane has thickened with diabetes-related deposits and because of endothelial cell proliferation, which is associated with pericyte degeneration. Basement membrane thickening and loss of pericytes are believed to result from low insulin and hyperglycemia, two important metabolic abnormalities of diabetes.

The neovascularization of PDR has been attributed to the subtle vascular abnormalities described above. Even this slight disruption may permit normally absent chemicals to enter the eye across the blood-retinal barrier. According to Sebag and McMeel, "Type I diabetics with rapidly deteriorating visual acuity due to proliferative and exudative retinopathy have elevated serum levels of IGF-I and -II." (citing Merimee et al. *N. Engl. J. Med* (1983) 309:527–30). "Very high serum levels of IGF-I have been reported in insulin-dependent diabetics with rapidly accelerating retinopathy." Ibid. "The concentration of IGF-I in the vitreous of most diabetic patients with severe neovascularization is elevated" (Brant et al., *Diabetes* (1986) 35:416–20). The concentration of IGF-I is high enough to stimulate cellular differentiation and growth in several assay systems. A positive correlation exists between the concentrations of IGF-I and IGF-II in vitreous and their concentrations in serum of diabetic subjects, but not in control subjects." (Wiedemann, *Survey of Ophthalmol.* (1992) 36:373–84). In an experimental model, IGF-I caused retinal neovascularization. (Mames et al., *Invest. Ophthalmol. Vis. Sci.* (1991) 32:754).

However, as Wiedemann points out, other growth factors appear to be involved, including fibroblast growth factors (FGF), TGF-β, an interplay of FGF and TGF-β, tumor necrosis factor (TNF-α and β), which are known to have angiogenic properties. *Wiedemann,* at 379–80. Still others have proposed that because retinal blood vessels appear to have a unique response to diabetic ischemia, there may be specific retina-derived growth factors. Berritault et al. *Diferentiation* (1981) 18:29–42; Chen and Chen *Invest. Ophthalmol. Vis. Sci.* (1980) 19: 596–02; D'Amore and Klagsburn *J. Cell. Biol.* (1984) 99: 1545–49; Elstow et al. *Invest. Ophthalmol. Vis. Sci.* (1985) 26:74–79; Glaser et al. *Ophthalmology* (1980) 87:440–46; and Ruelius-Altemose et al. *Invest. Ophthalmol. Vis. Sci.* (1985) 26 (ARVO Suppl):25.

According to Frank (*Ophthalmology* (1991) 98:586–93), "some cases of 'florid' proliferative retinopathy . . . may respond to hypophysectomy," which eliminates the release of growth hormone and curbs the release of IGFs.

According to Grant et al. (*Curr. Eye Res.* (1990) 2:323–35), the theory that IGF contributes to formation of diabetic retinopathy "is based on three observations: 1) in advanced stages of vascular proliferation, IGF-I concentrations in the vitreous of diabetics are greater than in controls, 2) serum and vitreous concentration of IGF-I correlate in diabetics but not controls, and 3) serum and vitreous IGF-I concentrations are substantially greater when proliferation is proceeding at a rapid rate."

Preretinal membranes from advanced cases of proliferative diabetic retinopathy and epiretinal membranes were removed from human eyes with retinal detachment with PVR and were analyzed using tracer antibody for IGF. IGF was found throughout the connective stroma, but in higher quantity around the inner walls of new blood vessels and around some fibroblast-like cells. Tissue from PVR eyes also disclosed IGF in the connective stroma and around fibroblast-like cells. This was interpreted as indicative of IGF-I promoting excessive cell proliferation. Fredj-Reygrobellet et al. *Ophthalmic Res.* (1991) 23:154–61.

Potential inhibitors of retinal angiogenesis have been sought. Tumor-induced angiogenesis was prevented with an extract of cartilage, which weighed about 16,000 daltons and inhibited protease activity. Langer et al. *Science* (1976) 193:70–71. Later studies indicated that normal vitreous humor contained such an inhibitor. For example, a vitreous protein with a molecular weight of 6200 was found to inhibit RDGF-induced proliferation and thymidine incorporation by vascular endothelial cells in vitro. Raymond and Jacobson, *Exp. Eye Res.* (1982) 34:267–86.

Clinically, the appearance of cotton wool spots in the retina signifies the onset of retinal ischemia. Sebag and McMeel, ibid. These spots are irregular patches of fibrous tissue.

Proliferative Vitreous Retinopathy (PVR)

According to Weller et al. (*Internatl. Ophthalmol.* (1990) 14:105–17), PVR is the eye's reaction to perforating trauma, retinal detachment and surgical manipulations.

Grant et al. (*Curr. Eye Res.* (1990) 9:323–35) applied IGF to human RPE cell cultures in the same quantities in which IGF had been found in the eyes of patients with PVR. RPE cells proliferated. After several days, "fibroblastic-like cells became apparent." Furthermore, IGF-I treatment increased chemotaxis significantly. This chemotactic response "could be totally blocked by the IGF-I receptor antibody," thus indicating the specificity of IGF-I for the chemotactic action. After IGF-I was withdrawn, the cells resumed more of an epithelial-like appearance. Based on their disclosure, Grant et al. "postulated that serum factors, including IGF-I, may be responsible in part for the initiation of cellular proliferation in [PDR] and PVR." (p. 333)

Weller et al. (Ibid.) believe that PVR is normal tissue repair with undesirable consequences for the retina and suggest that ophthalmic surgeons could control the repair process with drugs such as steroids and cytotoxic drugs.

What is needed is control of the repair process in the eye without systemically impairing an individual's infection-fighting ability and/or shutting down all cell proliferation.

Cataracts

Cataracts are opacities in what should be perfectly clear lenses. Cataracts interfere with the vision by causing blurred vision, glare, altered color perception and monocular diplopia. They are related to a variety of factors, including x-ray exposure and metabolic diseases such as diabetes, Wilson's disease (copper accumulation) and galactosemia. Cataracts are also a side effect of cortisone, methotrexate and nitrogen mustard therapy. According to McAvoy and Chamberlain, explants from newborn rat lenses showed significant cell proliferation when exposed to IGF-I. However, only a small amount of β-crystallin accumulated and in only a few cells. *Prog. Growth Factor Res.* (1990) 2: 29–44. IGF-1 has also been shown to enhance the EGF-induced initiation of DNA synthesis by corneal endothelial cells in cultured embryonic human eye globes (Hyldahl, *J. Cell. Sci.* (1986) 83:1–21). To date, no method of blocking cataract formation or progression has been found.

Corneal Epithelial Wounds

The cornea and conjunctiva are vulnerable to direct trauma, drying associated with disorders of tearing, exposure to radiant energy (ultraviolet light, sun and welding guns), allergens such as pollen and mold, and infectious agents. The cornea is associated with refractive errors.

Keratoconjunctivitis occurs in many individuals but is particularly associated with Stevens-Johnson syndrome, Wegener's granulomatosis, rheumatoid arthritis, atopic dermatitis and cicatricial pemphigoid. Corneal ulcers may occur. Causative organisms are herpes, other viruses and bacteria, although "sterile" ulcers also are observed, usually in association with a wound.

Normally, the cornea heals rapidly. FGF is known to be involved in the proliferation of corneal epithelial cells and scleral fibroblasts. IGF and FGF have a synergistic effect on fiber differentiation. IGF-2 is believed to encourage fetal scleral development but effects later in life have not been reported.

A method of enhancing healing of corneal epithelial wounds without scarring would help maintain vision.

Sjögren's Syndrome

Sjögren's syndrome is an immune system disorder which manifests itself in the eyes as conjunctival and corneal dryness (keratoconjunctivitis sicca syndrome) with a gritty sensation in the eyes. This is due to lack of tears following destruction of the lacrimal (or tear) glands by progressive mononuclear cell infiltrate and scarring of the gland. If the cornea is too dry, corneal ulcerations can develop.

"There is currently no effective treatment for the ongoing exocrine gland destruction. Treatment is geared toward symptomatic relief of mucosal dryness . . . and includes artificial tears [and] ophthalmologic lubricating ointments." *Harrison's Principles of Internal Medicine,* 12th ed., McGraw-Hill, pages 1449–50, 1991.

The ophthalmic disorders described above all lack optimal treatment.

Disclosure of Invention

In accordance with one embodiment of the present invention, there is provided a method for treating an individual with an ophthalmic disorder associated with an IGF excess. The method provides administering oral, topically or systemically to an individual an insulin-like growth factor binding protein (IGFBP). The IGFBP is administered in an amount sufficient to complex with free IGF and thereby alleviate the IGF excess.

In accordance with another embodiment of the present invention, the ophthalmic disorder is characterized by excessive fibrosis.

In accordance with a further embodiment of the present invention, the ocular disorder is selected from the group consisting of proliferative vitreoretinopathy, retinal wounds, macular degeneration, secondary cataracts, corneal epithelial wounds and Sjögren's syndrome. In a further embodiment, IGFBP is administered by intraocular injection or by application to the cornea. IGFBP can be applied to the cornea by means of eyedrops or a timed release capsule placed in the cul de sac.

In yet another embodiment, the method of the present invention provides IGFBP as IGFBP-3. In a further embodiment, the IGFBP-3 is recombinant human IGFBP-3.

In another embodiment, the individual to whom the complex is administered is a mammalian individual.

In yet another embodiment, the method provides for administration of the IGFBP complex in an amount sufficient to produce a decrease in fibroproliferation or in the symptoms due to excessive fibroproliferation. In a further embodiment, the amount of IGFBP-3 administered is at least about 3 μg to 3 mg per eye.

While not wishing to be bound by any particular theory, the Inventors propose that the administered IGFBP complexes with free IGF and results in a reduction in the free and immediately active IGF that was in excess. The lower level of free IGF lessens the stimulatory effect on the tissue in the eye which is responsible for fibroproliferation. The decrease in fibroproliferation or prophylaxis of fibroproliferation diminishes symptoms associated with fibroproliferation.

Modes For Carrying Out the Invention

Definitions:

"Insulin-like growth factor (IGF)" comprises a family of factors, including but not limited to IGF-I and IGF-II. IGF is a polypeptide having a molecular weight of about 7500 daltons. IGF can be obtained from natural sources or prepared by recombinant means.

"IGF excess" varies with the tissue, but it is generally the presence of more than a trace of free IGF (i.e., IGF not complexed with IGFBP). IGF often is excessive in diabetics.

"Fibroproliferation" refers to the production of fibrous tissue. In excess, it can cause excessive scarring such as occurs in PVR.

"Insulin-like growth factor binding protein (IGFBP)" comprises a family of binding proteins, including but not limited to IGFBP-1, IGFBP-2, IGFBP-3, IGFBP-4, IGFBP-5 and IGFBP-6. IGFBP can be obtained from natural sources or prepared by recombinant means. At least one form of IGFBP (for example, IGFBP-3) complexes with IGF and with a third molecule known as ALS.

"Ophthalmic disorder" refers to physiologic abnormalities of the eye. They may involve the retina, the vitreous humor, lens, cornea, sclera or other portions of the eye, or physiologic abnormalities which adversely affect the eye, such as inadequate tear production. The specific ophthalmic disorders intended herein are those treatable with IGFBP.

"Proliferative vitreoretinopathy" is characterized by the proliferation of excessive and/or unwanted fibroblasts or myofibroblasts, which are believed to be stimulated by IGF. Administered IGFBP complexes with excess IGF and helps control IGF interaction with these fibroblasts. IGFBP can thus moderate the formation of fibrous tissue.

"Retinal wounds" include, but are not limited to, tears and holes in the retina and separation from the underlying choroid. Retinal wounds appear after trauma, cystic degeneration, vitreoretinal traction, myopic degeneration, laser photocoagulation, lightning strike, pilocarpine administration and cataract extraction. As the retina heals, an excess of IGF may occur during part of the process. Administration of IGFBP aids healing of a variety of retinal wounds, because it complexes with free IGF and modulates the healing process.

"Macular degeneration" is characterized by the excessive build-up of fibrous deposits in the macula and retina and the atrophy of the retinal pigment epithelium. The administration of IGFBP can help limit excessive fibroproliferation and modulate the healing process by complexing with excess IGF.

"Macular holes" involve a degeneration of the macula which involves the full or partial thickness of the retina and may be surrounded by a halo of retinal detachment. Partial holes have a partial depth or only a partial circle, such as a new-moon or horseshoe shape. While the partial holes are not as visible, both full-thickness and partial holes can be treated with IGFBP, which complexes with any IGF present and modulates its action on the healing process.

"Secondary cataracts" are opacities in the ocular lens which interfere with vision. Secondary cataracts occur after x-ray exposure, in diabetes, Wilson's disease and galactosemia, and as side effects in drug therapy. IGFBP can be used to treat or prevent the development of secondary cataracts by complexing with IGF and moderating the IGF action of causing cell proliferation.

"Corneal epithelial wounds" includes damage to the cornea by a variety of causes including, but not limited to, trauma, dry eyes (in which the conjunctiva on the inside of the eyelid may abrade the cornea), and to excessive light, allergens and infectious agents. IGFBP can be used to treat corneal epithelial wounds by complexing with IGF and moderating the IGF action of causing epithelial cell replacement.

"Sjögren's syndrome" is an autoimmune disorder which frequently is characterized by dry eyes, due to destruction of the tear glands by the autoimmune process. IGFBP can be used to control at least the ocular manifestations of Sjögren's syndrome. While not wishing to be bound by any particular theory, it appears that first IGFBP may inhibit scarring of the tear gland by complexing with excess IGF and moderating the fibroproliferative process and that second, IGFBP also modulates healing of corneal epithelial wounds which arise from the dry eye syndrome caused by lack of tear glands.

A "therapeutic composition" as used herein is defined as comprising the IGF binding protein IGFBP-3. The therapeutic composition can also contain excipients such as water, minerals and carriers such as protein.

"Individuals" are defined as humans and mammal and avian farm animals, sport animals and pets. Farm animals include, but are not limited to, cows, hogs, sheep, chicken, turkeys, ducks and geese. Sport animals include, but are not limited to, dogs and horses. The category pets includes, but is not limited to, cats, dogs, and birds.

While not wishing to be bound by any particular theory, the Inventors propose that the administration of IGFBP increases the available pool of IGFBP and causes more IGF to complex with IGFBP. Then there is less free IGF available to interact with cellular IGF receptors and less stimulation of the production of fibrous tissue.

The method of the present invention contemplates treating ophthalmic disorders with IGFBP. IGFBP can be any of IGFBP-1, -2, -3, -4, -5 or -6. IGFBP also can be a mixture of any combination of the six IGFBP's. Such a mixture would take advantage of the different binding affinities for IGF-I and IGF-II, the ability of some IGFBP's to bind to cell surfaces, and the different half-lives of IGFBP's.

The molecular structure of IGFBP-1 was disclosed by Brewer et al., *Biochem. Biophys. Res. Comm.* (1988) 152 (3):1289–1297 and by Drop et al. in PCT Publication No. WO 89/98667, published on Sep. 21, 1989. Human IGFBP-1 has 234 amino acids and a molecular weight of about 28 kd. In combination with IGF-I, IGFBP-1seems to stimulate thymidine incorporation into cellular DNA. Busby et al., *Biol. Chem.* (1988) 263:14203–10; Elgin et al., *Proc. Natl. Acad. Sci. USA* (1987) 84:3254–58. Drop et al. (ibid.) suggested that IGFBP-1 would be useful in tissue repair because of its potentiation of growth of connective tissue and muscle cells.

IGFBP-2 comprises 289 amino acids (human) and has a molecular weight of 36 kd under nonreducing conditions. The amino acid sequence of human IGFBP-2 was determined from cDNA clones isolated from a human fetal liver library by Binkert et al. *EMBO J.* (1989) 8:2493–2502. IGFBP-2 also may bind to cell surfaces. IGFBP-2 has a preference for IGF-II and thus is used in formulations with IGF-II.

Preferably the IGFBP in the IGF/IGFBP complex is IGFBP-3. Native and recombinant IGFBP-3, as well as some N-terminal and C-terminal fragments, bind IGF-I and IGF-II. Human IGFBP-3 comprises 264 amino acids and has three potential N-linked glycosylation sites. IGFBP-3 is the major IGFBP in blood.

Nearly all IGF-I or IGF-II in blood is bound to IGFBP-3, and IGF/IGFBP-3 normally circulates in the form of a complex in humans and other mammals and avians. This complex associates with a third protein (ALS), which is present in excess over the concentration of IGF and IGFBP-3. Therefore, ALS is found both associated with the IGF/IGFBP-3 complex and in the free form. The resultant ternary complex has a size of about 150 kD. Administration of IGFBP-3, either from natural or recombinant sources, complexes with endogenous IGF-I and IGF-II and thence with ALS, which is normally in excess.

IGFBP-4 and IGFBP-6 are glycosylated proteins which are widely distributed in the body. The primary structure of IGFBP-4 was reported by Shimasaki et al. *Mol. Endocrinol.* (1990) 4:1451–1458. IGFBP-6, whose cDNA has been isolated by Shimasaki et al. (*Mol. Endocrinol.* (1991) 4:938–48), has a much greater affinity for IGF-II than for IGF-I. Hence IGFBP-6 may be preferable in situations of IGF-II excess.

IGFBP-5 is a 252 amino acid protein which is not glycosylated. Shimasaki et al. (*J. Biol. Chem.* (1991) 266:10646–53) cloned human IGFBP-5 cDNA from a human placenta library.

Depending on the binding, metabolic and pharmacokinetic characteristics required in the IGFBP formulation, these binding proteins can be used in various proportions.

The formulation, method of administration and dosage will depend upon the disorder to be treated, the point at which the disorder is being treated, and perhaps other aspects of the medical history of the patient. These factors are readily determinable in the course of therapy. Suitable patients with an ophthalmic disorder can be identified by medical history, physical findings and laboratory tests. The medical history reveals such facts as time of onset of symptoms such as red sclera, pain, photophobia, dry or gritty eyes, and vision changes, such as blurred vision not correctable with eyeglasses and double vision in an eye. Patients sometimes complain on inability to engage in their usual activities, such as watching television or driving a car at night.

Patients with ophthalmic disorders associated with IGF excess may have physical findings such as injected sclera, cotton-wool spots on the retina, a macular hole, bleeding behind the retina. Indicative laboratory results include high levels of IGF (free and bound) in the serum or in eye fluids, such as the vitreous.

Patients at risk for ophthalmic healing problems include those who have undergone surgery. Examples of such surgery include, but are not limited to, Cataract extraction, with or without lens replacement;

Corneal transplant or other penetrating procedures, such as penetrating keratoplasty (PKP);

Glaucoma filtration surgery;

Radial keratotomy; and

Other types of surgery to correct refraction.

The cornea provides the external optically smooth surface to transmit light into the eye. Surgery disrupts the forces which anchor the cornea in its normal configuration. In cataract patients, a full-thickness surgical incision is made in the region of the limbus. As the cornea heals, it contracts causing a local distortion of the tissue and a concomitant distortion in the visual field in the affected region (astigmatism).

Other surgical wounds in the cornea can initiate a wound healing process which causes a predetermined local shift in the curvature of the cornea. The most widely known of these techniques is radial keratotomy (RK), in which several partial-thickness incisions are produced to cause central corneal flattening. This technique, however, is limited due to a lack of predictable results and significant fluctuations in vision, both of which are related to the nature and extent of wound healing. Jester et al., *Cornea* (1992) 11: 191. For example, a reduction in peripheral bulging of the corneal tissue with an associated regression in the initial visual improvement has been observed in most RK patients. McDonnell and Schanzlin, *Arch. Ophthalmol.* (1988) 106: 212. Wounds in the cornea also heal slowly, and incomplete healing tends to be associated with instability of visual acuity (with fluctuations in vision from morning to evening, as well as drifting visual acuity occurring over a period of weeks to months). This may be the cause of 34% of patients who have had radial keratotomy complaining of fluctuating vision one year after surgery. Waring et al., *Amer. J. Ophthalmol.* (1991) 111: 133.

Also, if a corneal wound fails to heal completely, a wound "gape" can occur leading to a progressive hyperopic effect. Up to 30% of patients having the RK procedure are afflicted with hyperopic shifts associated with wound gape. Dietz et al., *Ophthalmology* (1986) 93: 1284. To make RK safer and more predictable, an agent which enhances wound healing can be used. In these conditions, the administration of IGFBP helps modulate the amount of free IGF and thereby control the healing process.

In accordance with the method of the present invention, the formulation comprises IGFBP with at least one pharmaceutically acceptable excipient.

In accordance with one method of the present invention, IGFBP is a human protein obtained from natural or recombinant sources. Most preferably, IGFBP is IGFBP-3 made by recombinant means and designated rhIGFBP-3. rhIGFBP-3 can be in glycosylated or non-glycosylated form. *E. coli* is a source of the non-glycosylated IGFBP-3. Glycosylated IGFBP-3 can be obtained from CHO-cells.

The method of the present invention provides for formulating the IGFBP-3 in modes which are readily apparent to those skilled in the art. Preferably, IGFBP is dissolved in physiologically compatible carriers such as normal saline solution or phosphate buffered saline solution.

Depending on the mode of administration, compositions of the IGFBP-3 can be solid, semi-solid or liquid preparations, such as for example, tablets, pills, powders, capsules, liquids, suspensions or the like. Dosage forms for gastrointestinal administration must be suitably coated and buffered to avoid gastrointestinal digestion of the protein. Physiologically compatible carriers include intravenous solutions, such as normal saline, serum albumin, 5% dextrose, plasma preparations, other protein-containing solutions and TPN solutions. The preferred carrier for parenteral administration of the complex is a sterile, isotonic aqueous solution, such as normal saline or 5% dextrose. Alternatively, a solution of the complex can be placed into an implant, such as an osmotic pump, for the slow release of the complex over an extended period of time. Alternatively, the IGFBP-3 can be provided in sustained release carrier formulations such as semi-permeable polymer carriers in the form of suppositories or microcapsules. See, for instance, U.S. Pat. No. 3,773,919 for Microcapsular Sustained Release Matrices Including Polylactides; Sidmon et al., *Biopolymers* 22 (1), 547–556 (1983) for copolymers of L-glutamic acid and γ-ethyl-L-glutamate; Langer et al., *J Biomed Res* 15, 167–277 (1981) for poly(2-hydroxyethylmethacrylate) or the like.

The mode of administration delivers the IGFBP-3 to the individual in a safe, physiologically effective manner. The IGFBP-3 is given by intranasal, subcutaneous, intravenous, intraperitoneal, or other conventional routes of administration. Preferably, the IGFBP-3 is injected subcutaneously, intravenously or intramuscularly. Most preferably, the IGFBP-3 is administered by subcutaneous injection. By subcutaneous injection, the IGFBP-3 appears not to be toxic or mitogenic at the injection site. In another preferred mode of administration, the IGFBP-3 is administered by continuous intravenous infusion in combination with TPN solutions.

The dose of IGFBP-3 to be administered can be readily determined by those skilled in the art, based on the usual patient symptoms discussed above. Preferably, when IGFBP is administered to humans daily, the dosage is at least about 3 μg to 3 mg per eye. More preferably, the daily dosage of IGFBP for humans is at least 0.1 mg/kg/day. If daily dosages in excess of about 0.5 mg/kg must be given, the dosage is divided and injected subcutaneously at two or more sites.

If IGFBP were administered to humans twice a week, each dose of IGFBP-3 is preferably at least about 0.1 mg/kg of body weight. More preferably, for twice weekly administration, the dose of the IGFBP-3 is at least 0.5 mg/kg. There is no known upper limit of dosage; however, it is preferable that a single dose not exceed 10 mg/kg of body weight, because higher doses may complex with too much IGF and interfere with its modulation.

Preferably, the patient is started with a relatively low dose of IGFBP, such as 0.05 mg/kg of body weight/day. The various factors given above should be monitored to determine if there is improvement. If the patient improves with the low dose, the low dose preferably should be continued until the patient's ophthalmic disorder is ameliorated or improved, as indicated by the physical findings and laboratory results described above. Such improvement should be evident in two to three weeks.

If the patient's symptoms do not improve significantly after the low dose of IGFBP, the dose preferably should be increased gradually until the improvement is noticeable.

Somewhat higher per kilogram doses are needed for small animals receiving IGFBP. For example, a bird can be dosed twice a week with about 0.05 to 1.0 mg/kg of body weight.

The invention has been disclosed by direct description. The following are examples showing the efficacy of the method in treating ophthalmic disorders. The examples are only examples and should not be taken in any way as limiting to the scope of the method.

EXAMPLES

Example 1
Treatment of Macular Holes

Patients with Stage 2, 3, and 4 macular holes are to be treated. First, at least two independent observers examine the eyes by biomicroscope to confirm the stage of the macular hole, according to the criteria of Gass (*Arch. Ophthalmol.* (1988) 106:629–39). Briefly, eyes with Stage 2 holes have retinal dehiscence along the margin of the area of deep retinal cyst formation. In Stage 3, typically there is a full-thickness hole with overlying operculum. Macular holes are classified as Stage 4 when a posterior vitreous detachment is present.

All eyes should have subjective decreases in visual acuity as well as subjective distortions of vision. Before treatment, technicians who were not told the planned treatment obtain best corrected Snellen visual acuity, measure intraocular pressure, photograph the fundus and perform fluorescein angiography.

Doses of 1 ng, 100 ng and 1,000 ng of IGFBP are administered. The low dose is at the low end of the effective range, and the highest dose is chosen to be within the expected range. Eyes are randomly chosen for a control or one of the treatment doses.

A standard three-port vitrectomy is to be performed on all test eyes. For eyes with Stage 2 and Stage 3 macular holes, a core vitrectomy is performed. In Stage 4, a complete pars plana vitrectomy is performed. When an epiretinal membrane is found, it is peeled from the retina and removed from the eye. If there is gelatinous condensation on the inner surface of the retina, this can be dissected free, but must be performed with great care to limit traction on the edges of the macular hole or damage to the nerves.

After a short time to allow peripheral fluid to drain posteriorly, any fluid that has migrated posteriorly can be aspirated. The center of the macular hole is gently aspirated to remove the last remaining amount of fluid around the macular hole.

A tapered, bent-tipped cannula is then connected to a 1 cc syringe containing a solution of IGFBP. About 0.1 cc of IGFBP solution is gently infused into the macular hole.

After surgery, patients must lie supine for the first 24 hours; thereafter, the patient should remain in a face-down position as much as possible over the next two weeks.

After surgery, patients are examined on day 1, at two weeks and at 4–6 weeks, and monthly thereafter. Fluorescein angiography is performed at 4–6 weeks, 3 months and 6 months. Best corrected Snellen visual acuity, intraocular pressure, lens status, bubble size, status of the macular hole and occurrence of adverse effects are determined at each examination.

On the first and second postoperative days, the anterior chamber has only trace amounts of flare and cells. Occasionally a fine, red-brown precipitate is found on the endothelial surface of the cornea with minimal striae. But these findings resolve within two weeks without sequelae. All eyes have bubbles filling at least 75% of the vitreous cavity on the first postoperative day. The bubble shrinks over time, to about 30–40% by the sixth week. By about the sixth week, eyes which will ultimately show improvement have a flattening of the detachment and thinning of the adjacent retina to a normal-appearing thickness. Eyes with such flattening usually have improvements in visual acuity. Angiographic findings can improve in eyes with flattening of the macula and surroundings.

Example 2

A cat corneal wound healing model is used to evaluate wound healing in the presence of IGFBP. In this model, two diametrically opposed partial-thickness (75–80% depth) incisions are made in the central cornea of cat eyes. One incision is the untreated control, and the other incision is dosed with a solution containing IGFBP-3. Doses are between 3 µg and 3 mg IGFBP per incision. After a suitable period of time for healing (e.g., T=0, 7, 14, 30, 90 and 180 days), the eyes are examined for astigmatism using a Computed Anatomy Corneal Modeling System or equivalent device. The extent of healing is determined by measuring wound tensile strength through burst pressure determinations. The incisions also are evaluated by analyses of representative histological sections of the treated and control incisions. In this model, improved wound healing is reflected as a reduction in astigmatism and/or increased tensile strength without undue (namely vision limiting) scar formation.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

We claim:

1. A method for treating an individual who has undergone or is about to undergo or is undergoing ophthalmic surgery to promote healing without vision limiting scarring, said method comprising administering to said individual insulin-like growth factor binding protein-3 (IGFBP-3), said IGFBP-3 being administered in an amount sufficient to promote healing without vision limiting scaring, wherein said amount is administered by local or topical administration at 3 µg to 3 mg per eye.

2. The method of claim 1, wherein the IGFBP-3 is administered by direct application in the surgical wound.

3. The method of claim 1, wherein the IGFBP-3 is administered by intraocular injection.

4. The method of claim 1, wherein the IGFBP-3 is recombinant human IGFBP-3.

5. The method of claim 1, wherein the ophthalmic surgery is cataract extraction.

6. The method of claim 1, wherein the ophthalmic surgery is a corneal transplant.

7. The method of claim 1, wherein the ophthalmic surgery is surgery to correct refraction.

8. The method of claim 7, wherein the surgery to correct refraction is radial keratotomy.

9. The method of claim 1, wherein the ophthalmic surgery is glaucoma filtration surgery.

10. The method of claim 6 wherein the ophthalmic surgery is keratoplasty.

11. A method for treating an individual who has undergone, is about to undergo, or is undergoing corneal transplant surgery, comprising locally or topically administering 3 µg to 3 mg insulin-like growth factor binding protein-3(IGFBP-3) to said individual.

12. The method of claim 11, wherein the administration is performed by administration to the cornea or sclera.

13. The method of claim 12, wherein the application to the cornea or sclera is placement of timed release dosage form in the cul-de-sac.

14. The method of claim 11, wherein said IGFBP-3 is recombinant human IGFBP-3.

* * * * *